United States Patent [19]
Garrett et al.

[11] Patent Number: 6,012,179
[45] Date of Patent: Jan. 11, 2000

[54] GARMENTS FOR CONTROLLING BODY TEMPERATURE

[75] Inventors: Michael E. Garrett, Woking, United Kingdom; Howard R. Miller, Chatham, N.J.

[73] Assignee: The BOC Group plc, Windlesham, United Kingdom

[21] Appl. No.: 08/778,457

[22] Filed: Jan. 3, 1997

[30] Foreign Application Priority Data

Jan. 5, 1996 [GB] United Kingdom .................... 9600175

[51] Int. Cl.$^7$ ...................................................... A61F 7/00
[52] U.S. Cl. .............................. 2/456; 2/DIG. 3; 607/104
[58] Field of Search ............................... 2/455, 456, 458, 2/81, DIG. 1, DIG. 3, 69; 62/259.3; 607/96, 104, 107, 108, 109, 110, 111, 112

[56] References Cited

U.S. PATENT DOCUMENTS

| | | | |
|---|---|---|---|
| 3,507,321 | 4/1970 | Palma | 165/46 |
| 3,648,764 | 3/1972 | Starr | 165/32 |
| 5,292,347 | 3/1994 | Pompei | 607/104 |
| 5,304,213 | 4/1994 | Berke et al. | 607/104 |
| 5,383,918 | 1/1995 | Panetta | 607/104 |
| 5,421,326 | 6/1995 | Rankin et al. | 128/201.19 |
| 5,443,488 | 8/1995 | Namenye et al. . | |
| 5,709,203 | 1/1998 | Gier | 128/201.21 |

FOREIGN PATENT DOCUMENTS

| | | | |
|---|---|---|---|
| 311336 | 4/1989 | European Pat. Off. | A61F 7/00 |
| 1 462 033 | 1/1973 | United Kingdom . | |
| 1 467 729 | 5/1974 | United Kingdom . | |

Primary Examiner—Gloria M. Hale
Assistant Examiner—Tejash D Patel
Attorney, Agent, or Firm—Philip H. Von Neida; Salvatore P. Pace

[57] ABSTRACT

A garment for use by a patient during an operation comprises an inner skin and an outer skin which between them define a space. A source and value are provided for passing a gas mixture of air and a predetermined volume of helium through the space to control the body temperature of the patient.

1 Claim, 1 Drawing Sheet

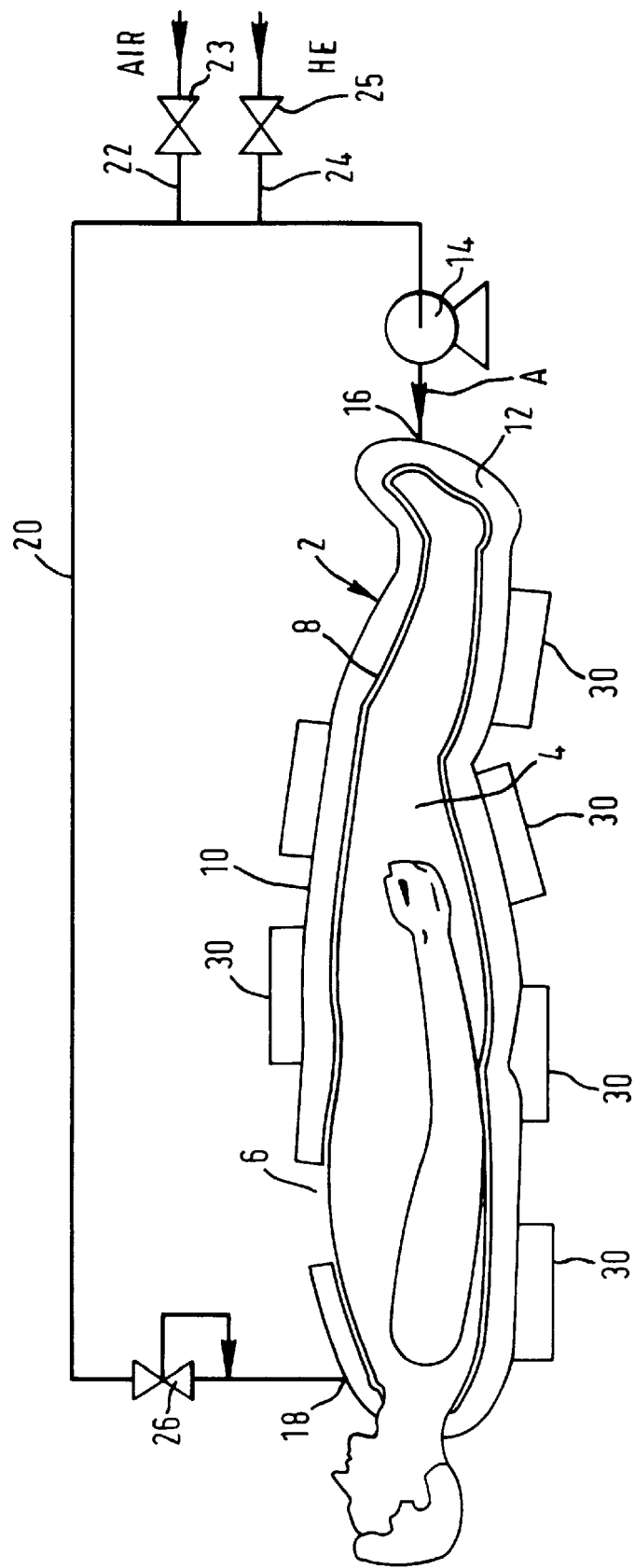

GARMENTS FOR CONTROLLING BODY TEMPERATURE

The present invention relates to methods of and garments for controlling the body temperature of patients.

BACKGROUND OF THE INVENTION

Some types of surgery, for example open-heart surgery, require that the patient's body should be cooled by several degrees from its normal body temperature to reduce the patient's metabolic rate. This gives the surgeon a longer period to work on organs where the blood supply may be limited or even cut off. Temperature regulation is also recognized as a major problem in pediatrics and neo-natal surgery.

In order to cool the body of a patient prior to an operation, the patient is usually anaesthetized and packed in ice to rapidly lower the body temperature. In certain circumstances, ice is placed inside the body cavity during an operation. This method, while providing rapid cooling of the patient's body temperature, offers no degree of control over the temperature drop of the patient's body during an operation. This problem is resolved in accordance with present invention by a garment which when worn by a patient during an operation, will enable a surgeon or other medical personnel to control the drop in body temperature.

SUMMARY OF THE INVENTION

According to the present invention, there is provided a garment for use by a patient undergoing surgery comprising an inner and outer skin, the skins defining between them a space, an inlet into and an outlet from said space and means for passing a gas mixture of air and a predetermined volume of helium through the space to control the body temperature of the patient.

BRIEF DESCRIPTION OF THE DRAWING

The FIGURE is a schematic view of a patient wearing a garment according to the present invention.

DETAILED DESCRIPTION OF THE INVENTION

The garment which provides an improved means of lowering the body temperature of a patient during surgery in a controlled manner is illustrated with reference to the FIGURE. As shown, a garment 2 for use by a patient 4 during an operation, covers in substance the body and limbs of a patient. Preferably, the garment includes at least one space or opening 6 to allow access to the patient about the area of the body or limbs where the operation is to be performed. The garment 2 includes an inner skin 8 and spaced therefrom an outer skin 10. The skins 8, 10 between them define a space 12. The space 12 forms part of a circuit for a gas mixture of air and a predetermined volume of helium. The circuit includes a pump 14, an inlet 16 for the gas mixture into the space 1 2 and an outlet 18 for the discharge of the gas mixture from the space 12 and a conduit 20 from the outlet 18 back to the pump 14.

Conduits 22, 24 extend from sources respectively of air and helium and are connected to the conduit 20 at a location upstream of the pump 14. The passage of air and helium flow through their respective conduits 22, 24 is controlled by valves 23, 25. A valve 26 is located in conduit 20 for evacuation of any gas mixture trapped in the space 12 after the operation has been concluded.

According to a further aspect of the present invention illustrated in the FIGURE, cooling means are positioned on or immediately adjacent the outer skin of the garment and pumping a gas mixture including air and a pre-selected volume of helium through the space defined by the skins. Preferably, the cooling means comprises at least one eutectic block.

The volume of helium in the mixture passing through the space defined by the skins will vary according to a number of factors including the surface area, temperature and body weight of the patient, the surface area of the cooling means and its temperature relative to that of the patient and the like. In given circumstances, helium will transfer approximately six times the amount of heat the same volume of air. On this basis, a volume mixture of 20% helium in air will double the rate of heat transfer and a mixture of 60% helium in air will quadruple.

Those skilled in the art will appreciate that, in accordance with the present invention, the amount of helium in the mixture may be initially high to rapidly lower the body temperature of the patient to the desired level, and then adjusted downward to reach an equilibrium so that the desired temperature is maintained. Hence, a pre-determined level of helium in the mixture at any point in time in the surgical procedure will be that level which is required to achieve or maintain the desired temperature of the patient. The increased thermal conductivity of the helium/air mixture in combination with sensitive sensing equipment provides an accurate control over the body temperature of the patient.

In use, just prior to an operation, the patient 4 is dressed in the garment 2 and laid out on an operating table. The inlet 16 and outlet 18 are connected to the remainder of the circuit in a manner known per se. In the embodiment illustrated in the FIGURE, eutectic blocks 30 are positioned on or immediately adjacent the outer skin 10 along the length of the body of the patient. Subsequently, a required gas mixture is fed from the respective sources through the conduits 22, 24 into the conduit 20 for passage through the space 12. The pump 14 pumps the selected gas mixture in the direction of arrow A through the inlet 16 space 12 and out through the outlet 18 and around the conduit 20 and back to the pump 14. Since helium exhibits a high thermal conductivity relative to air, the percentage by volume of helium in the gas mixture will determine how much cold from the eutectic blocks 30 is transmitted through skin 10, the gas mixture in the space 12 and skin 8 to cool a patient. The more helium that is circulating between the skins 8, 10 the greater will be the rate of cooling of the patient's body. It is envisaged that the temperature of the patient will be constantly monitored and an electrical or electronic signal fed to control means for automatically controlling the settings of valves 23, 25 in order to adjust the temperature of the patient by adjusting the percentage by volume of helium in the gas mixture.

Clearly, although eutectic blocks 30 have been used as an example to describe the cooling means, other means could be provided for providing the cold for reducing the body temperature of the patient.

We claim:

1. A method for controlling the body temperature of a patient comprising the steps of placing the patient in a garment having an inner and an outer skin, the skins defining between them a space, positioning a cooling source comprising at least one eutectic block immediately adjacent the outer skin of the garment, pumping a gas mixture including air and a pre-selected volume of helium through the space defined by the skins, and controlling the percentage by volume of helium in the gas mixture to control the thermal conductivity of the mixture and the cold transmitted through space.

* * * * *